(12) United States Patent
Gambert et al.

(10) Patent No.: US 6,416,715 B1
(45) Date of Patent: Jul. 9, 2002

(54) DEVICE FOR COLLECTING AND RELEASING SALIVA

(75) Inventors: Rudolf Gambert, Wismar; Norbert Neubauer, Halberstadt; Kerstin Wex, Wismar, all of (DE)

(73) Assignees: IT Dr. Gambert GmbH, Wismar; Primed Halberstadt Medizintechnik GmbH, Halberstadt, both of (DE)

(*) Notice: Subject to any disclaimer, the term of this patent is extended or adjusted under 35 U.S.C. 154(b) by 0 days.

(21) Appl. No.: 09/530,501

(22) PCT Filed: Sep. 4, 1998

(86) PCT No.: PCT/EP98/05603

§ 371 (c)(1),
(2), (4) Date: Apr. 28, 2000

(87) PCT Pub. No.: WO99/22645

PCT Pub. Date: May 14, 1999

(30) Foreign Application Priority Data

Oct. 31, 1997 (DE) .......................................... 197 48 331

(51) Int. Cl.⁷ .................................................. B01L 3/02
(52) U.S. Cl. ...................... 422/100; 422/101; 422/102; 422/99
(58) Field of Search ................................ 422/100, 101, 422/102, 99; 600/573, 580; 128/760; 604/317, 224

(56) References Cited

U.S. PATENT DOCUMENTS

| | | | |
|---|---|---|---|
| 4,418,702 A | * 12/1983 | Brown et al. | ............... 128/760 |
| 4,709,705 A | 12/1987 | Truglio | |
| 4,852,620 A | 8/1989 | Jakubowicz et al. | |
| 5,268,148 A | * 12/1993 | Seymour | ..................... 422/101 |
| 5,376,337 A | * 12/1994 | Seymour | ..................... 422/101 |
| 5,393,496 A | * 2/1995 | Seymour | ..................... 422/101 |
| 5,494,646 A | * 2/1996 | Seymour | ..................... 422/101 |
| 5,910,122 A | * 6/1999 | D'Angelo | ................... 600/573 |

FOREIGN PATENT DOCUMENTS

| | | |
|---|---|---|
| CA | 2077528 | 3/1994 |
| WO | 94/04078 | 3/1994 |
| WO | 95/02996 | 2/1995 |
| WO | 95/08761 | 3/1995 |

* cited by examiner

*Primary Examiner*—Jill Warden
*Assistant Examiner*—Brian Sines
(74) *Attorney, Agent, or Firm*—Jordan and Hamburg LLP

(57) ABSTRACT

This invention relates to a device for collecting and releasing saliva. The purpose of the invention is to provide sample device which is easy and safe to handle and which is configured as a disposable construction for use especially on medical diagnostics. To this end, the device consists of a porous unit which can take up the sample fluid and can be squeezed out. The unit is located inside a container which is sealed on one side at one end, and is arranged in such a way that it can be displaced out of said container at the other end which can be opened. The end of the container which can be opened is provided with a sealing cap.

37 Claims, 3 Drawing Sheets

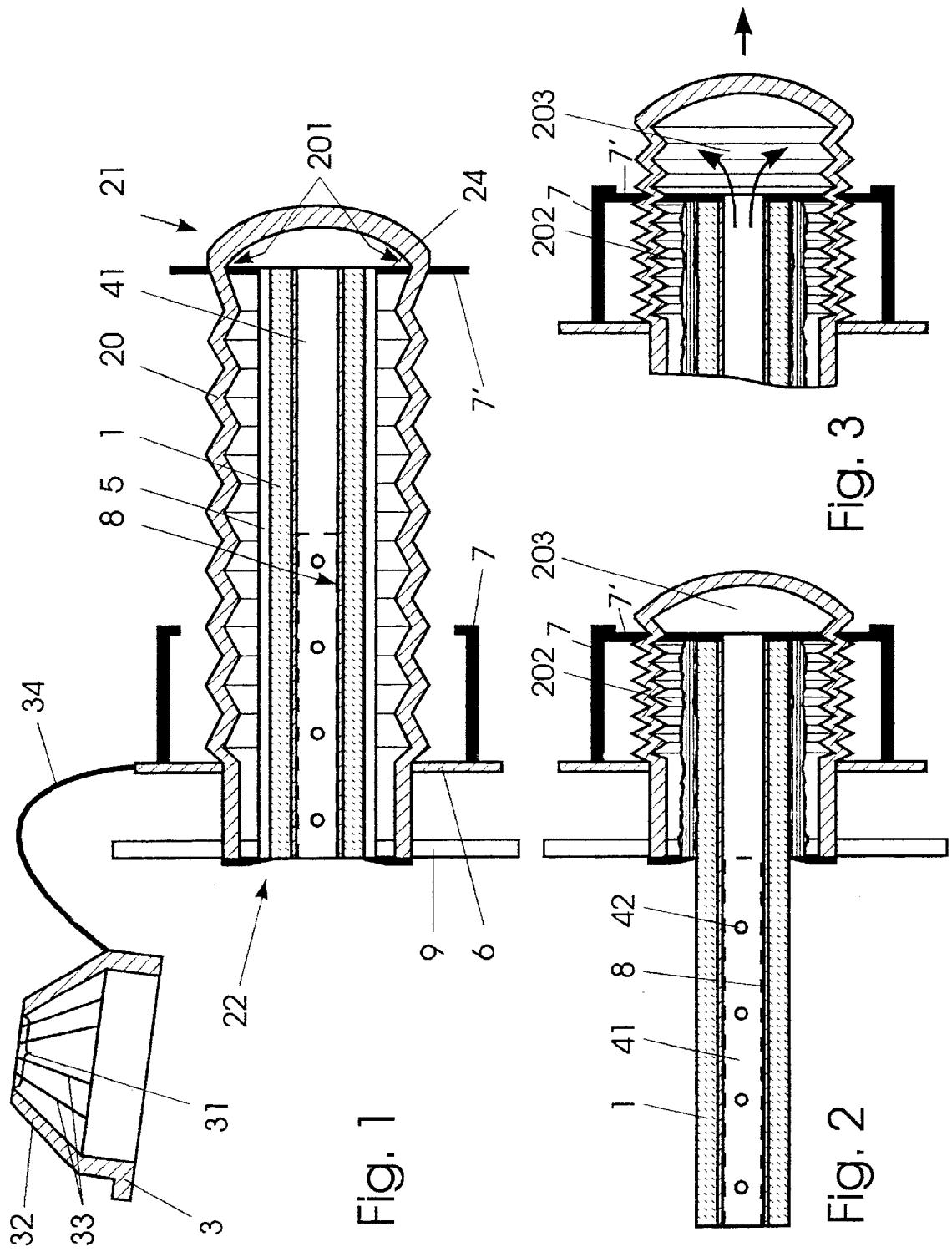

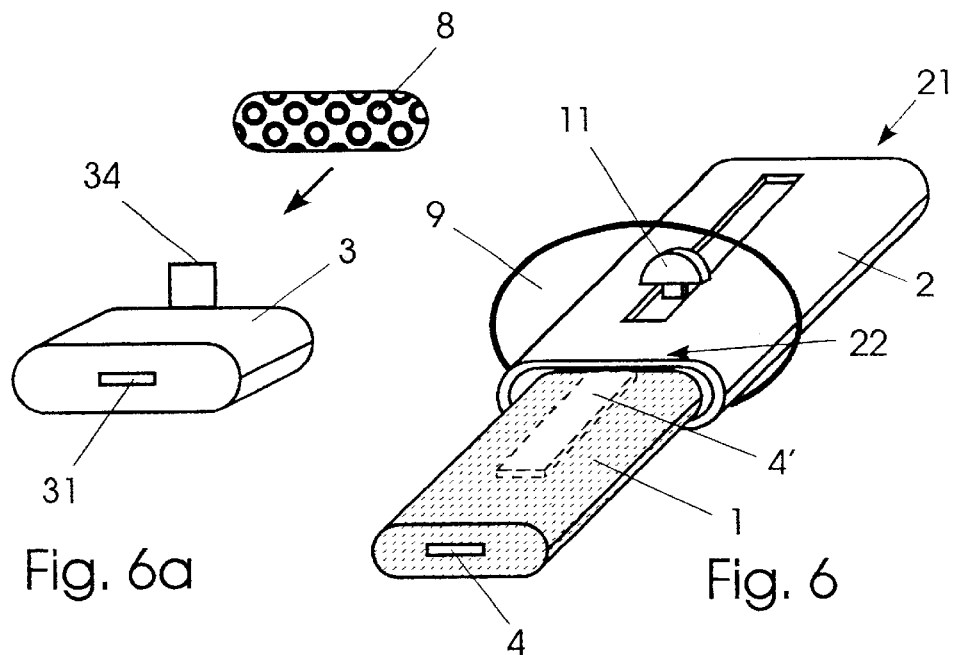
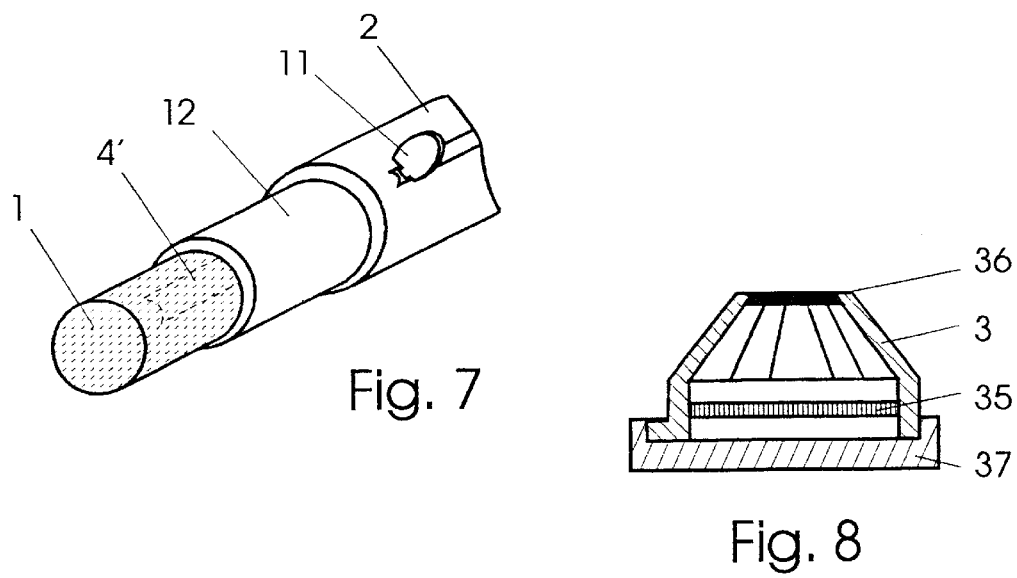

DEVICE FOR COLLECTING AND RELEASING SALIVA

BACKGROUND OF THE INVENTION

The invention relates to a device for collecting and releasing saliva for diagnostic purposes.

In the prior art, there are devices and methods, respectively, known in the field of art. So in DE 36 32 303 A1 a chewable, absorbent, elastic, and inert profiled body is placed in the mouth of a proband until said body is penetrated with saliva. Then the body is placed in a centrifuge tube which, at its bottom, is provided with openings through which the saliva escapes in the course of centrifugation so that it is available for further examinations. In EP 0 520 408 A1 there is described a sample device for collecting saliva and other fluid exudations that comprises a sample receptacle with an indicator and a reaction fluid. A special embodiment of the sample receptacle described there is provided with a body made of a porous mass which is adapted to collect the sample fluid and the reagent fluid and which can be squeezed out by a plunger. Due to the fact that the desired chemical reaction or the application of a buffer solution for the saliva sample is carried out within the entire device, in which simultaneously a sample analysis has to be performed, the device design is comparatively expensive so that it is too cost-intensive for a one-off use only. Similar devices have been described in, for example, U.S. Pat. No. 5,268,148, WO 95/02996, and WO 94/04078.

SUMMARY OF THE INVENTION

It is an object of the present invention to provide a device for collecting and releasing saliva that permits a simple and safe handling and is designed as a disposable unit, in particular for diagnostic purposes, whereby the risk of contamination both of the sample to be collected and for the personnel handling the device is substantially obviated.

The object is realized by the features of the first claim. Advantageous embodiments are covered by the dependent claims.

DETAILED DESCRIPTION OF THE INVENTION

Figure 4:
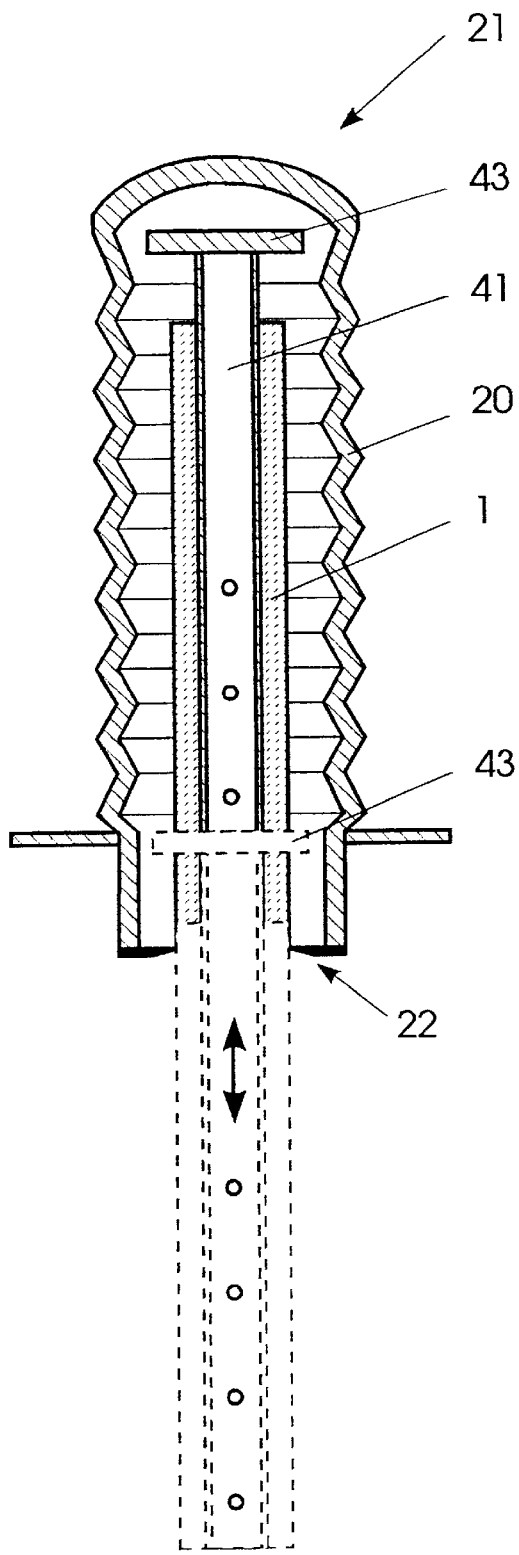
Figure 5:
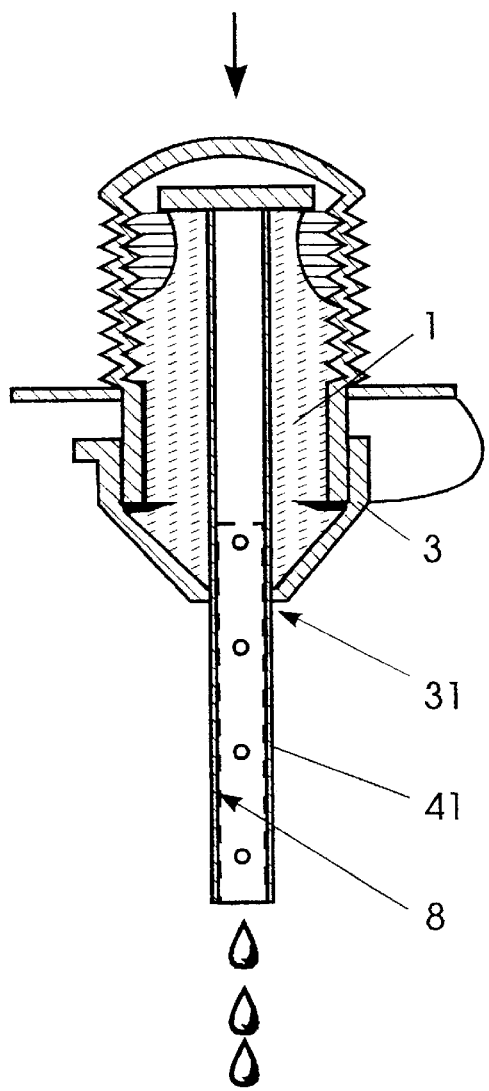

The invention will be described hereinafter in more detail by reference to the schematical embodiments. There is shown in:

FIG. 1 a lateral section of a first embodiment in an initial position before use, FIG. 2 the embodiment of FIG. 1 in service position for receiving saliva or any other sample fluid, FIG. 3 a lateral partial section of a modified embodiment of FIG. 1 in a service position, FIG. 4 a lateral section of a second embodiment in both, an initial position and in a service position, FIG. 5 an end position according to FIG. 4 in which the collected saliva or the sample fluid is released, FIG. 6 a perspective view of a third embodiment in a service position, FIG. 6a a locking cap for an embodiment according to FIG. 6, FIG. 7 a view, partially perspective, of a fourth embodiment in a service position, and FIG. 8 a special embodiment of the locking cap.

FIG. 1 shows a first embodiment of a device for collecting and releasing saliva or other sample fluids. The device comprises a porous unit 1 adapted to be squeezed out that consists of polyurethane, water-catalyzed polyurethane, polyethylene, polypropylene or cellulose. Said porous unit 1 is displaceably arranged in a receptacle, in the present example in a bellow 20. The bellow 20 is provided with a closed end-portion 21 and an end-portion 22 that can be opened. A locking cap 3 is adapted for fitting on said end-portion 22. The interior wall of the porous unit 1 is provided with a supporting means which, in the present example, is embodied by a drainage tube 41. Openings 42 are circumferentially distributed over a part of said drainage tube 41. Furthermore, the porous unit in the present example is externally enclosed by a hose-like foil 5. The locking cap 3 used herein comprises a conic mouthpiece 32, the interior wall of which is provided with capillary grooves 33. The device is put into a service position by removing the locking cap 3 which is connected to the bellow 20 in that the bellow 20 is seized at a flanged handle 6 by two fingers of one hand while the thumb presses upon the closed end-portion 21 of the bellow. Thereby the porous unit 1 and the drainage tube 41 supporting the former is slidingly moved out of the bellow 20, whereas the hose-like foil 5 is slidingly pushed together in the interior of the bellow 20 by the action of respective counteractive means or by being bonded to the base ranges of the bellow. The service position described is shown in FIG. 2. The porous unit 1 is then placed in a not shown mouth of a proband and takes up there a quantum of saliva necessary for further tests. Additionally the porous unit 1 can be impregnated with a substance for stimulating salivation and/or with a test agent for indicating, for example, drugs. In order to define a preselected insertion depth, the bellow 20 and the receptacles represented in the following embodiments, respectively, can additionally be provided with an oral stop plate 9.

Furthermore, the bellow 20 can be provided with means 7, 7' that, in the compressed state of the bellow, are interlocked. When sufficient saliva has been taken up, the locking mechanism 7, 7' is released and when there is employed an elastic one for the bellow 20, the porous unit 1 and the drainage tube 41 are retracted into the bellow 20 provided that the drainage tube 41 is brought into a rigid connection with the interior wall 201 of the bellow in the range of the closed end-portion 21 of the bellow. Preferably said rigid connection 24 circumferentially seals the interior wall 201 of the bellow so that two chambers 202 and 203 result to which different pressure can be applied. When the rigid connection 24, as represented in FIG. 3, is somewhat moved off from the closed end-portion 21 of the bellow, the volume of the chamber 203 is increased in such a manner that when only relieving this part of the bellow an underpressure is produced, as indicated by the arrows in FIG. 3, whereby the porous unit 1 is still better humidified by saliva throughout.

In FIG. 4 a second embodiment is represented with substantial features of FIG. 1 in common. Here, however, in contrast to FIG. 1, the bellow 20 is inelastically embodied, the drainage tube 41 is not rigidly connected to interior wall 201 of the bellow and the porous unit 1 is not enclosed by a hose-like foil 5. Herein the drainage tube 41 is only provided with a stop 43 at the interior side of the bellow. In this example, after removal of the locking cap, not shown in FIG. 4, the porous unit 1 together with the supporting drainage tube 41 is only shaken out of the bellow 20 by force of gravity and brought into the position of service, shown in dash-lines. The dimensions of the stop are such that the latter remains within the bellow 20 even in the position of service. In the following, the procedure is in analogy to FIG. 1. After sufficient saliva has been taken up the porous unit 1 with the drainage tube 41 supporting the former is moved back again into the bellow. Then the locking cap 3 is put on. The device, which now contains a sample fluid (saliva), can now be fed into an analysis device, not shown in detail. To this end and in the same manner pressure is applied to the devices according to FIG. 1 and FIG. 2, as indicated by an arrow in FIG. 5. For this purpose the locking cap 3 is provided with an open aperture 31 or with an aperture which will now be opened. The feasibility of closing the aperture 31 is given to the end that the sample fluid in the receptacle is additionally provided with a buffer solution or has already been provided with a reagent and has to be transported or stored. In each case, however, the geometry of the aperture 31 is so designed that it corresponds to the cross-section of the supporting means, which is here the drainage tube 41, and only permits the passing through of the latter when pressure is applied whereas the porous material remains in the bellow 20 where it is compressed whereby the sample fluid is passed into the analysis device via the protruding drainage tube 41. Advantageously, the drainage tube as described in the embodiment up to here can be provided on its interior wall, with respect to the molecular weight of the sample fluid, with a selective filter 8.

FIG. 6 shows a simplified embodiment, which lies within the scope of the invention, that comprises a receptacle 2 with a closed end portion 21, respectively with an end portion 21 adapted to be tightly sealed. The receptacle 2 has a sleeve, not shown in detail, slidingly engaged within said receptacle 2. Said sleeve is adapted to receive a porous unit 1 that is, according to FIG. 6, of oval-shaped cross-section. A supporting means 4 is inserted into the unit 1 and a supporting means 4', respectively, is worked into the upper circumference of the unit 1. A locking cap 3, separately shown in FIG. 6a, is connected via a connecting tongue 34 to the unlockable end-portion 22 of the receptacle 2. In the case of the supporting means 4 being centrally inserted and rigidly connected to a slider 11, the locking cap 3 is also provided with an aperture 31, the geometry of the same is adapted to the cross-section of the supporting means 4. It is, however, also feasible to design the embodiment in such a manner that, for example, a circular aperture 31 is provided wherein the opening of the same is not adapted to the cross-section of the supporting means 4. Then the supporting means 4 is not able to pass through the aperture 31 when the slider 11 is slidingly advanced and the porous unit 1 is compressed. In this case a suitable passage facility for the supporting means 4 has to be provided at the bottom of the not shown sleeve, thus ensuring that said supporting means remains in the receptacle 2 while the porous unit 1 is compressed. At such an embodiment a selective filter 8 can be fitted into the locking cap 3. Also in this embodiment the locking cap 3 can be designed conically and in analogy to that represented in FIG. 1. The handling of the present embodiment is in analogy to that described in connection with FIGS. 1 to 5.

FIG. 7 shows a perspective partial view of a further embodiment that largely corresponds to that described in FIG. 6, apart from the fact that here the porous unit 1 is of circular cross-section and the further components are adapted to this geometry. In FIG. 7 the sleeve 12, not shown in more detail in FIG. 6, is overdrawn in an enlarged view.

Furthermore, with all the embodiments described, in which at least the closed end portion 21 of the receptacle is designed optically transparent, the invention suggests within its scope to impregnate with a test agent and/or with an indicator at least that portion of the porous unit 1, which lies within the range of the closed end portion of the receptacle. As a result thereof and, for example, due to color change, it is feasible to optically indicate a sufficient amount of sample fluid required.

In all those cases in which the porous unit 1 is not provided with a supporting means, the locking cap 3 can be further designed in an embodiment as it is indicated by example of FIG. 8. Said embodiment is designed in such a way that the locking cap 3 is provided, on the one hand, with a filter 35 that permits passage of the sample fluid with the locking cap put on and when the porous unit is compressed and, on the other hand, with a filter 36 permeable to gas that prevents the passage of the sample fluid. Thereby the locking cap itself is adapted to be filled with a sample fluid, it can be removed after cutting through the connecting tongue 34, closed by a cover 37, and stored separately. In this case, it lies within the scope of the invention to impregnate the filter 35 with a substance that, for example, preserves the saliva sample (for example, a biocide such as sodium azide), the pH-value of which buffers off, the surface tension of which reduces and complexes metal ions in the saliva sample. It lies within the frame of such a design to provide any further test agents within the locking cap. Furthermore, the outer shape of the locking cap 3 can be so designed that it can be directly inserted into a conventional analysis device.

All the embodiments represented are, due to their setup, disposable devices, in particular, for a rapid medical diagnosis by which, however, their application is not restricted. In the same way they can be used in receiving and releasing any desired sample fluids.

All features disclosed in the specification, in the subsequent claims, and in the drawing are substantial for the invention both, individually and in any combination with one another.

List of Reference Numerals

1 porous unit
2 receptacle
20 bellow
201 interior wall of bellow
202, 203 chambers under different pressure
21 closed end-portion of receptacle
22 unlockable end-portion of receptacle
24 rigid connection
3 locking cap
31 aperture
32 conic mouthpiece
33 capillary grooves
34 connecting tongue
35 filter for sample fluid
36 filter permeable to gas
37 cover
4 supporting means
41 drainage tube
42 openings
43 stop
5 hose-like foil
6 flanged handle
7, 7' locking means
8 selective filter
9 oral stop-plate
11 slider
12 sleeve

What is claimed is:

1. A device for collecting and releasing a sample fluid comprising:
    a porous unit for collecting the sample fluid and releasing the sample fluid when said porous unit is compressed;
    a receptacle for displaceably accepting said porous unit, said receptacle having an open end-portion and a closed end-portion;

a slide mechanism for displacing a portion of said porous unit out of and back into said receptacle through the open end-portion; and a locking cap engageable at said open end-portion for dispensing the sample fluid when the slide mechanism is displaced, with the locking cap in place at said open end-portion, and the porous unit is compressed against the locking cap thereby expelling the sample fluid.

2. A device for collecting and releasing a sample fluid comprising:

a porous unit for collecting the sample fluid and releasing the sample fluid when said porous unit is compressed;

a receptacle for displaceably accepting said porous unit, said receptacle having an open end-portion and a closed end-portion;

a slide mechanism for displacing a portion of said porous unit out of and back into said receptacle through the open end-portion;

a locking cap engageable at said open end-portion for dispensing the sample fluid when the slide mechanism is displaced, with the locking cap in place at said open end-portion, and the porous unit is compressed against the locking cap thereby expelling the sample fluid; and a supporting device arranged within said porous unit to support said porous unit when displaced from said receptacle.

3. The device as claimed in claim 2, wherein said supporting device is a drainage device.

4. The device as claimed in claim 3, wherein said porous unit is displaceably arranged for movement relative to said supporting device.

5. A device for collecting and releasing a sample fluid comprising:

a porous unit for collecting the sample fluid and releasing the sample fluid when said porous unit is compressed;

a receptacle for displaceably accepting said porous unit, said receptacle having an open end-portion and a closed end-portion;

a slide mechanism for displacing a portion of said porous unit out of and back into said receptacle through the open end-portion; and a locking cap engageable at said open end-portion for dispensing the sample fluid when the slide mechanism is displaced, with the locking cap in place at said open end-portion, and the porous unit is compressed against the locking cap thereby expelling the sample fluid;

said locking cap having an aperture for dispensing the sample fluid when the sample fluid is expelled from the porous unit; and a supporting device, said aperture having a cross section corresponding to a cross-section of said supporting device whereby said aperture permits passage of said supporting device.

6. The device as claimed in claim 5, wherein said locking cap is tapered toward said aperture.

7. The device as claimed in claim 6, wherein said locking cap has grooves on an internal surface.

8. A device for collecting and releasing a sample fluid comprising:

a porous unit for collecting the sample fluid and releasing the sample fluid when said porous unit is compressed;

a receptacle for displaceably accepting said porous unit, said receptacle having an open end-portion, and including a displaceable member for displacing at least a portion of said porous unit, upon application of force on said displaceable member, out of the open end-portion of said receptacle; and a locking cap at said open end-portion for dispensing the sample fluid when said displaceable member is displaced to compress said porous unit against said locking cap thereby expelling the sample fluid from the porous unit;

wherein said receptacle includes a bellows and said displaceable member is a closed end of said bellows.

9. The device as claimed in claim 8, wherein said bellows is elastically embodied.

10. The device as claimed in claim 8, said bellows is inelastically embodied.

11. The device as claimed in claim 2, further comprising a foil enveloping said porous unit.

12. The device as claimed in claim 9, wherein a drainage device is connected to an interior wall of the bellows at the closed end of said receptacle.

13. The device as claimed in claim 12, wherein said bellows further comprises a first and second chamber and a rigid connection circumferentially engaging said interior wall of said bellows and separating said first and second chambers whereby said first and second chambers are provided with different pressure when a force acts upon the bellows to induce an underpressure.

14. The device as claimed in claim 1, wherein said receptacle further comprises a flanged handle at the open end-portion of the receptacle.

15. The device as claimed in claim 9, wherein said device further comprises a flanged handle at the open end-portion of the receptacle, wherein the flanged handle and the closed end of the bellows each comprise a latching device for latching the flanged handle and the closed end to each other when the bellows is in a compressed state.

16. The device as claimed in claim 1, wherein said porous unit is formed from polyurethane, water-catalyzed polyurethane, polyethylene, polypropylene or cellulose.

17. The device as claimed in claim 1, wherein said porous unit further comprises a substance for stimulating salivation.

18. A device as claimed in claim 1, wherein said porous unit further comprises an indicator.

19. The device as claimed in claim 1, further comprising a selective filter for filtering a selected molecular weight of said sample fluid.

20. The device as claimed in claim 1, wherein said locking cap is separable from the device for collecting and releasing a sample fluid.

21. A device for collecting and releasing a sample fluid comprising:

a porous unit for collecting the sample fluid and releasing the sample fluid when said porous unit is compressed;

a receptacle for displaceably accepting said porous unit, said receptacle having an open end-portion and a closed end-portion;

a slide mechanism for displacing a portion of said porous unit out of and back into said receptacle through the open end-portion;

a locking cap engageable at said open end-portion for dispensing the sample fluid when the slide mechanism is displaced, with the locking cap in place at said open end-portion, and the porous unit is compressed against the locking cap thereby expelling the sample fluid; and a selective filter for filtering a selected molecular weight of said sample fluid;

wherein said locking cap has an outer end and an inner end opposite the open end-portion of the receptacle when the locking cap is in a closed position on the open end-portion of the receptacle, a fluid filter, said fluid filter permitting passage of the sample fluid and a gas permeable filter, said gas permeable filter being permeable to gas and preventing a passage of the sample fluid.

22. The device as claimed in claim 21, wherein said locking cap is provided at the outer end of the locking cap with a cover, said cover being closeable.

23. The device as claimed in claim 1, wherein said locking cap has an aperture for dispensing the sample fluid when the sample fluid is expelled from the porous unit.

24. A device for collecting and releasing a sample fluid comprising:
- a porous unit for collecting the sample fluid and releasing the sample fluid when said porous unit is compressed;
- a receptacle for displaceably accepting said porous unit, said receptacle having an open end-portion, and including a displaceable member for displacing at least a portion of said porous unit, upon application of force on said displaceable member, out of the open end-portion of said receptacle; and
- a locking cap at said open end-portion for dispensing the sample fluid when said displaceable member is displaced to compress said porous unit against said locking cap thereby expelling the sample fluid from the porous unit.

25. The device as claimed in claim 8 further comprising a supporting device arranged within said porous unit to support said porous unit when extended from said receptacle.

26. The device as claimed in claim 25, wherein said supporting device is a drainage device.

27. The device as claimed in claim 26, wherein said porous unit is displaceably arranged for movement relative to said supporting device.

28. The device as claimed in claim 8, further comprising a foil enveloping said porous unit.

29. The device as claimed in claim 8, wherein said porous unit is formed from polyurethane, water-catalyzed polyurethane, polyethylene, polypropylene or cellulose.

30. The device as claimed in claim 8, wherein said porous unit further comprises a substance for stimulating salivation.

31. The device as claimed in claim 8, wherein said porous unit further comprises an indicator.

32. The device as claimed in claim 8, further comprising a selective filter for filtering a selected molecular weight of said sample fluid.

33. The device as claimed in claim 8, wherein said locking cap is separable from the device for collecting and releasing a sample fluid.

34. The device as claimed in claim 32, wherein said locking cap has an outer end and an inner end opposite the open end-portion of the receptacle when the locking cap is in a closed position on the open end-portion of the receptacle, a fluid filter, said fluid filter permitting passage of the sample fluid and a gas permeable filter, said gas permeable filter being permeable to gas and preventing a passage of the sample fluid.

35. The device as claimed in claim 24, wherein said locking cap is provided at the outer end of the locking cap with a cover, said cover being closeable.

36. The device as claimed in claim 8, wherein said locking cap has an aperture for dispensing the sample fluid when the sample fluid is expelled from the porous unit.

37. The device as claimed in claim 36, wherein said locking cap has an aperture for dispensing the sample fluid when the sample fluid is expelled from the porous unit.

* * * * *